United States Patent [19]

Smith

[11] 4,327,228
[45] Apr. 27, 1982

[54] 3-NITRO-1-PHENYL-1-(M-CHLORO-PHENYL)-PROPAN-2-OL.

[75] Inventor: Paul Smith, Hoddesdon, England

[73] Assignee: Beecham Group Limited, England

[21] Appl. No.: 156,189

[22] Filed: Jun. 3, 1980

[30] Foreign Application Priority Data

Jun. 14, 1979 [GB] United Kingdom ............... 20746/79

[51] Int. Cl.³ .............................................. C07C 4/00
[52] U.S. Cl. ............................... 568/705; 260/501.18; 564/319
[58] Field of Search ................... 564/319; 260/501.18; 568/705

[56] References Cited

U.S. PATENT DOCUMENTS

| 1,356,877 | 10/1920 | Nagai | 568/705 X |
| 1,973,647 | 9/1934 | Nagai | 568/705 X |
| 3,431,272 | 3/1969 | Loev | 568/705 X |
| 3,859,354 | 10/1975 | Booher et al. | 568/705 X |
| 3,932,663 | 1/1976 | Barrett | 564/319 X |

FOREIGN PATENT DOCUMENTS 83574  8/1971  German Democratic Rep. ..................................... 564/320

OTHER PUBLICATIONS

Henning et al., "Helv. Chim. Acta.," vol. 59, No. 6, pp. 2213–2217 (1976).
Houben–Weyl, "Methoden der Organischen Chemie", vol. 11, No. 1 pp. 385–391 (1957).
Wagner et al., "Synthetic Organic Chemistry", p. 664 (1953).
Rainer et al., "Chemical Abstracts", vol. 85, p. 465, Section No. 1767544 (1976).

Primary Examiner—Robert V. Hines
Attorney, Agent, or Firm—Jacobs & Jacobs

[57] ABSTRACT

A process for the preparation of 3-dimethylamino-1-phenyl-(m-chlorophenyl)propan-2-ol and its salts which comprises the Raney nickel catalysed reduction of 3-nitro-1-phenyl-(1-m-chlorophenyl)propan-2-ol with simultaneous or subsequent dimethylation and thereafter, if desired, salification.

1 Claim, No Drawings

3-NITRO-1-PHENYL-1-(M-CHLOROPHENYL)-PROPAN-2-OL.

British patent specification No. 1443441 disclosed inter alia that 3-dimethylamino-1-phenyl-1-(m-chlorophenyl)propan-2-ol and its pharmaceutically acceptable salts were useful mood modifying agents. The synthesis disclosed in the said specification is tedious and gives rather low overall yields of the desired product. It is clearly desirable to find a more effective synthesis. A synthesis providing higher yields has now been discovered.

The present invention provides a process for the preparation of 3-dimethylamino-1-phenyl-1(m-chlorophenyl)propan-2-ol and its salts which comprises the Raney nickel catalysed reduction of 3-nitro-1-phenyl-1-(m-chlorophenyl)propan-2-ol with simultaneous or subsequent dimethylation and thereafter, if desired, salification.

In general for a rapid reaction, an elevated pressure of hydrogen is employed, such as 100 to 400 p.s.i, more suitably 200 to 300 p.s.i, for example 250 p.s.i. (gauge pressures). Lower pressures, for example an atmospheric pressure, may be used but these lead to slower reactions.

On a weight basis, the ratio of Raney nickel employed to nitro compound to be reduced is from 2:1 to 1:10 more suitably from 1:1 to 1:4, for example about 1:2.

The temperature of reaction is suitably 0° C. to 120° C., more suitably 10° C. to 40° C. and most conveniently at ambient temperature.

A solvent such as a lower ($C_{1-4}$) alkanol, for example ethanol, is generally used. Other suitable solvents include aqueous lower alkanols.

The presence of an acid such as acetic acid during the reduction results in the preparation of a salt of the amine.

If the dimethylamino compound is to be produced *in situ* then formaldehyde, for example as formalin, may be included in the hydrogenation.

If it is desired to methylate the primary amine subsequent to reduction this may be effected by reaction with formic acid and formaldehyde. Such reactions are generally effected at elevated temperature, for example at reflux point if excess formic acid and formaldehyde are used as solvent.

3-Nitro-1-phenyl-1-(m-chlorophenyl)propan-2-ol may be prepared according to this invention by the reaction of m-chlorophenyl-phenylacetaldehyde with nitromethane in the presence of an alkali metal hydroxide.

The alkali metal hydroxide used is most suitably sodium or potassium hydroxide of which potassium hydroxide is preferred.

The reaction is generally carried out using a lower ($C_{1-4}$) alkanol as solvent, for example ethanol or methanol. The reaction is best started at a depressed temperature such as −10° C. and then allowed to proceed at approximately ambient temperature such as 18°–28° C.

In a preferred process aspect this invention provides a process for the preparation of 3-dimethylamino-1-phenyl-(m-chlorophenyl)propan-2-ol or a pharmaceutically acceptable salt thereof which process comprises:
(a) the reaction of m-chlorophenyl-phenylacetaldehyde with nitromethane in the presence of a base to yield 3-nitro-1-phenyl-1-(m-chlorophenyl)propan-2-ol
(b) reducing the 3-nitro-1-phenyl-1-(m-chlorophenyl)propan-2-ol with hydrogen in the presence of Raney nickel to yield 3-amino-1-phenyl-1-(m-chlorophenyl)propan-2-ol or its salt and (c) dimethylating the 3-amino-1-phenyl-1(m-chlorophenyl)propan-2-ol or its salt to yield 3-dimethylamino-1-phenyl-1-(m-chlorophenyl)propan-2-ol or its salt.

In the above process, stages (b) and (c) can be carried out sequentially in the same reaction vessel, for example by including formaldehyde as a methylating agent in the reduction mixture.

This invention also provides 3-nitro-1-phenyl-1-(m-chlorophenyl)propan-2-ol. 3-Nitro-1-phenyl-1-(m-chlorophenyl)propan-2-ol is useful in the hereinbefore described processes.

The 3-dimethylamino-1-phenyl-1-(m-chlorophenyl)-propan-2-ol hydrochloride produced by the process of this invention can exist in various polymorphic forms. A polymorphic form favoured because of its storage stability can be obtained by recrystallisation from ethanol/toluene mixtures or by heating in toluene. Once obtained this favoured form may be formulated as described in British patent specification No. 1443441, the disclosures of which are incorporated herein by reference.

The following Examples illustrate this invention:

EXAMPLE 1

3-Nitro-1-phenyl-1-(m-chlorophenyl)propan-2-ol

A solution of potassium hydroxide in methanol (5% w/v; 243 ml) was cooled to −8° C. and nitromethane (12.5 ml) added with stirring. After 5 minutes a solution of m-chlorophenyl-phenylacetaldehyde methanol (50 g; 0.22 M in 200 ml) was added slowly in order to keep the temperature below 0° C. The solution was left at 0° C. for 30 minutes, allowed to come to room temperature over 2 hours and evaporated under reduced pressure to give a yellow oil. This was partitioned between water and ether (approx. 200 mls. of each) and the water layer acidified to pH 6 with acetic acid and extracted with ether (3×200 ml). The ether layers were combined, dried ($Na_2SO_4$), filtered and evaporated to give the nitro-alcohol as an orange-yellow oil (44 g; 70%). (This was used directly in the next step).

EXAMPLE 2

3-Amino-1-phenyl-1-(m-chlorophenyl)propan-2-ol-acetate

Crude 3-nitro-1-phenyl-1-(m-chlorophenyl)propan-2-ol (43 g; 0.15 M) in ethanol (600 ml) containing acetic acid (9.3 ml:1 equiv.) and RaNi (approx. 20 g.,) was hydrogenated at 250 p.s.i. $H_2$ pressure for 4 hours. The mixture was filtered and evaporated to give a greenish oil. Trituration with ether (250 ml) gave the required product (34 g; 72%) as an off-white solid M.pt. 132°–137° C.

EXAMPLE 3

3-Dimethylamino-1-phenyl-1-(m-chlorophenyl)propan-2-ol hydrochoride

3-Amino-1-phenyl-1-(m-chlorophenyl)propan-2-ol acetate salt (30 g; 0.09 M) was added to a mixture of formic acid (30 ml) and formaldehyde (40% formalin) (30 ml) and refluxed for 3½ hours. After cooling, the solution was poured onto a rapidly stirred mixture of potassium carbonate solution and ether. The ether layer was separated, washed with water, dried (Na$_2$SO$_4$) and ethereal HCl added. After leaving for 12 hours at 0° C. the solid was filtered, collected and recrystallised from ethanol/ether to give the title compound (26 g; 86%) M.pt. 185°–186° C. (softens at 120° C.).

EXAMPLE 4

3-Dimethylamino-1-phenyl-1-(m-chlorophenyl)propan-2-ol hydrochloride

Crude 3-nitro-1-phenyl-1-(m-chlorophenyl)propan-2-ol (45 g:0.15 M) in ethanol (600 ml), containing acetic acid (9.5 ml:1 equiv.), 40% Formalin (45 ml) and RaNi (approx. 20 g.) was hydrogenated at 250 p.s.i. H$_2$ pressure for 5 hours. The mixture was filtered and evaporated to give a green coloured oil. The oil was washed with water, dried (Na$_2$SO$_4$) and ethereal HCl added. A little ethanol was added to help crystallisation of the hydrochloride and the mixture left 12 hours at 0° C. The pale green solid was collected and recrystallised from EtOH/Et$_2$O to give the title compound (29.8 g; 59%) as a white solid. M.pt 185°–186° C. (softens at 120° C.).

EXAMPLE 5

3-Dimethylamino-1-phenyl-1-(m-chlorophenyl)propan-2-ol hydrochoride—Favoured Polymorph (a) 3-Dimethylamino-1-phenyl-1-(m-chlorophenyl)-propan-2-ol hydrochloride (35 g ex. EtOH/Et$_2$O) was recrystallised from a mixture of ethanol (200 ml) and toluene (300 ml). The resulting polymorph had the X-ray spectral characteristics set out in (c) below.

(b) 3-Dimethylamino-1-phenyl-1-(m chlorophenyl)-propan-2-ol hydrochloride (48 g ex. EtOH/Et$_2$O) were suspended in toluene (500 ml) and heated under reflux for 10 minutes with stirring. The solution was allowed to cool to ambient temperature and the resultant crystals filtered off, washed with a little diethylether and dried under vacuum to yield 46 g of the polymorph having the X-ray spectral characteristics set out in (c) below.

(c) The positions of significant X-ray powder diffractogram lines are given for material ex. EtOH/Et$_2$O and ex. toluene. The positions are taken from traces X470 and 508 respectively and are given in °2$\theta$ using Copper K$_\alpha$ radiation.

(Form I) 5.7, 7.8, 9.4, 11.3, 12.4, 15.8, 16.0, 16.8, 17.0, 18.4, 20.5, 21.5, 22.2, 23.6, 24.7, 26.0, 27.6, 29.2, and 31.0.

(Form II) 8.0, 12.4, 13.5, 14.5, 16.0, 16.5, 17.4, 18.2, 18.8, 20.7, 21.3, 22.2, 23.3, 24.0, 25.3 (shoulder) 25.7, 26.9, 28.0, 28.4, 29.7, 30.3, and 31.8.

What we claim is:

1. 3-Nitro-1-phenyl-1-(m-chlorophenyl)propan-2-ol.

* * * * *